United States Patent [19]

Lyman

[11] Patent Number: 4,770,854

[45] Date of Patent: Sep. 13, 1988

[54] LABORATORY FLASK

[75] Inventor: George F. Lyman, Rocky Point, Me.

[73] Assignee: Costar Corporation, Cambridge, Mass.

[21] Appl. No.: 825,442

[22] Filed: Feb. 3, 1986

[51] Int. Cl.$^4$ ............................................. C12M 1/24
[52] U.S. Cl. .................................. 422/102; 435/284; 435/296; 435/298; 215/10; 215/31
[58] Field of Search ............... 422/102; 435/240, 284, 435/296, 298; 215/6, 365, 10, 31, 228; 220/DIG. 12, DIG. 13, DIG. 14; D24/9, 23, 29, 31

[56] References Cited

U.S. PATENT DOCUMENTS 3,449,210  6/1969  Rohde ........................... 435/298 X 4,334,028  6/1982  Carver ............................. 435/284

OTHER PUBLICATIONS

Fisher Scientific 1983, Allied, (1983), p. 1187.
The Lab Book, Corning, (1984), pp. 220–221.

Primary Examiner—Barry S. Richman
Assistant Examiner—Jill Johnston
Attorney, Agent, or Firm—Wolf, Greenfield & Sacks

[57] ABSTRACT

A laboratory flask includes a body and a canted neck at one end joined to the main surface by an inclined ramp. The neck diameter is maximized and along with the ramp allows the user excellent accessibility to the four corners of the flask end wall with a pipette and to the four corners of the growing surface with a scraper.

26 Claims, 3 Drawing Sheets

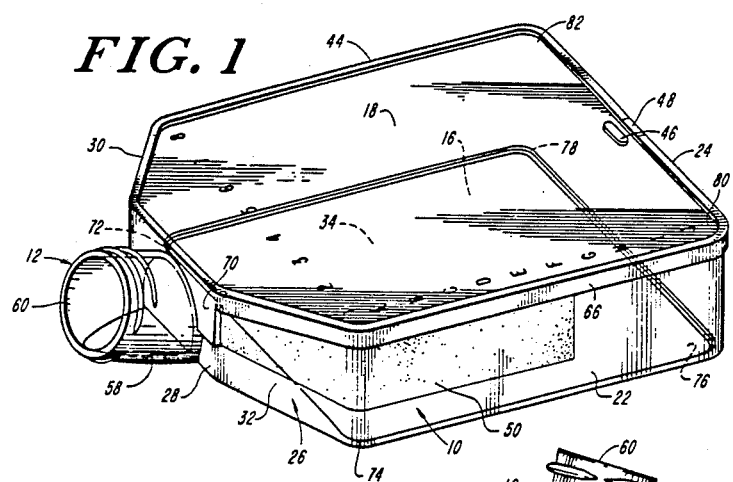
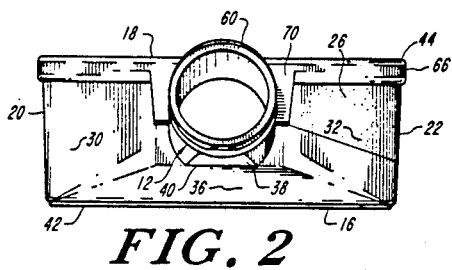
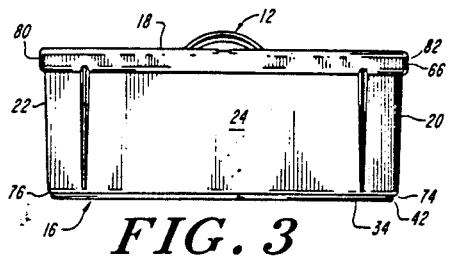
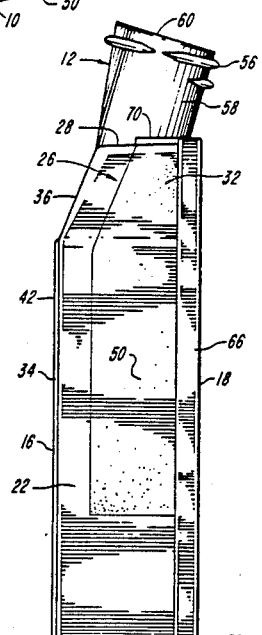
FIG. 1
FIG. 2
FIG. 3
FIG. 4

LABORATORY FLASK

INTRODUCTION

This invention relates to laboratory flasks and more particularly comprises a new and improved flask for growing cell and tissue cultures.

Culture flasks are widely used in the laboratory for a variety of purposes. In normal use, cell and tissue culturing occurs in agar or in medium, which covers the bottom wall. During testing the cultures are frequently visually examined while growing in the flasks, and frequently the cultures are removed by a scraper and the medium by a pipette.

The principal object of the present invention is to enable the laboratory technician to perform these functions more easily and efficiently. More specifically, one object of this invention is to provide a flask shape which enables the user to reach the entire bottom surface of the flask, including the corners, with a scraper so that cultures may be removed. Another object of the invention is to enable a pipette to reach the four corners of the end wall of the flask remote from the flask neck so that medium may be removed without disturbing the botton growing surface. Another object of this invention is to improve the flask shape so that fluid may most conveniently be poured from it. Yet another object of this invention is to shape the flask in such a way as to minimize medium spill. And another object of this invention is to provide means to enable a user to locate and identify specific areas in the flask so as to simplify microscope work. Still another object of this invention is to reduce the shelf space required for a number of flasks.

To accomplish these and other objects, the flask of this invention includes among its features an extra wide neck and ramp to provide excellent access for a scraper or pipette to the corners of the bottom and end walls, respectively. Alpha-numeric coordinates are provided on the top wall of the flask to identify the areas of the bottom wall when viewed through the top wall. A stacking facility is built into the top and bottom walls to enable identical flasks to be stacked one on top of the other. A shoulder region is formed in the flask which provides excellent pouring.

These and other objects and features will be better understood and appreciated from the following detailed description of one embodiment thereof, read in connection with the accompanying drawings.

BRIEF FIGURE DESCRIPTION

FIG. 1 is a perspective view of a laboratory flask with its screwcap removed, constructed in accordance with this invention;

FIG. 2 is a front view thereof;

FIG. 3 is a rear view thereof;

FIG. 4 is a side view thereof, with the flask standing on end;

DETAILED DESCRIPTION

Figure 5:
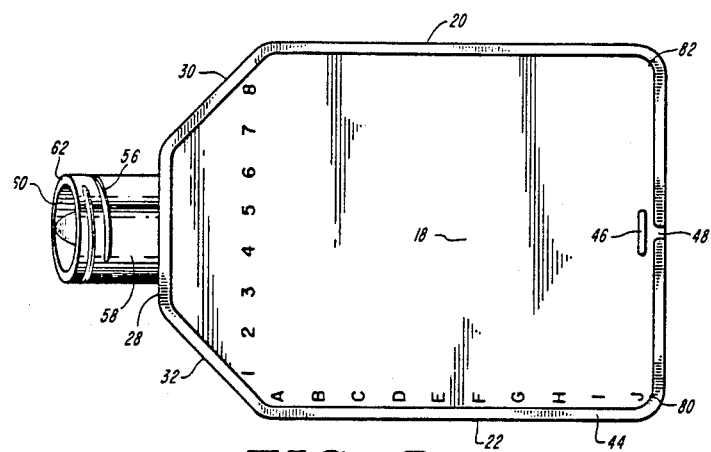
FIGS. 5 and 6 are top and bottom plan views thereof, respectively.

The laboratory flask shown in the drawing includes a body 10, a neck 12 and a removable coverall screwcap 14. In this specification, the flask will be described in the orientation shown in FIG. 1 when referring to top, bottom, sides etc. but it is, of course, understood that the flask is not limited in any way to that particular position.

The body 10 has a bottom wall 16 and a top wall 18 that generally lie in parallel planes, and they are connected together by side walls 20 and 22, and first and second end walls 24 and 26. The neck 12 is integrally formed with the central section 28 of the second end wall 26. The second end wall 26 also includes diverging portions 30 and 32 which extend from the ends of the central portion 28 to the side walls 20 and 22, respectively. The top wall 18 is essentially flat throughout its full extent. The bottom wall 16 throughout its major rectangular portion 34 is flat and parallel to the top wall 18 while the remaining portion 36 of the bottom wall defines an inclined ramp from the neck 12 to horizontal, rectangular portion 34 of the bottom wall. The ramp 36 is disposed in an angle of approximately 22° with the horizontal while the margins of the ramp defined by the end wall portions 30 and 32 diverge from one another in an angle of approximately 90° (90° is the included angle between walls 30 and 32. Each wall is 45° from the central line.) for purposes which will be described below.

Figure 6:
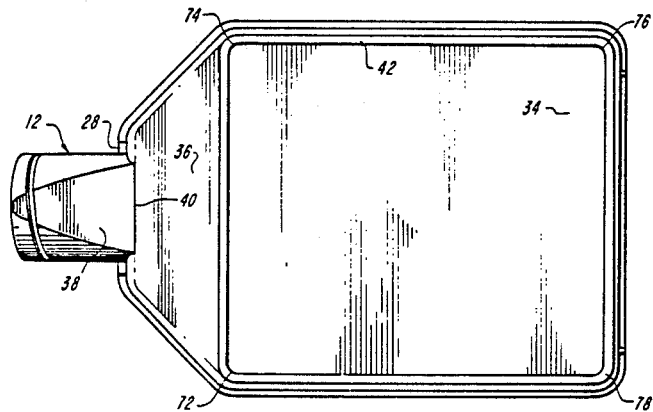

The neck 12 as shown in FIGS. 2 and 6 is provided with a flat lower surface 38 which intersects the ramp 36 along line 40. The angle of the flat 38 is approximately 8 degrees to the horizontal so that the intersection 40 defines the juncture between two dissimilar slopes. Nevertheless, both the flat 38 and the ramp 36 slope downwardly toward the major portion 34 of the bottom wall 16 so that any fluid on the flat 38 will tend to flow into the interior of the flask.

Figure 7:
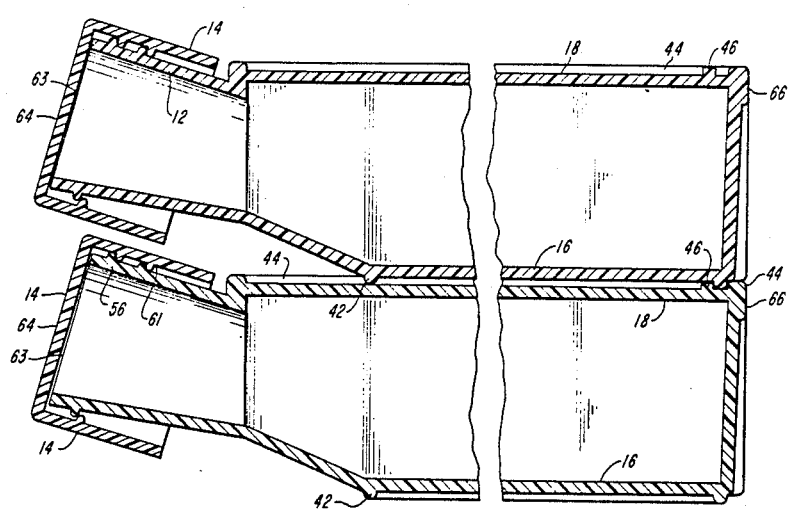
FIG. 7 is a side view of two identical flasks with their caps in place, stacked one upon the other.
Figure 8:
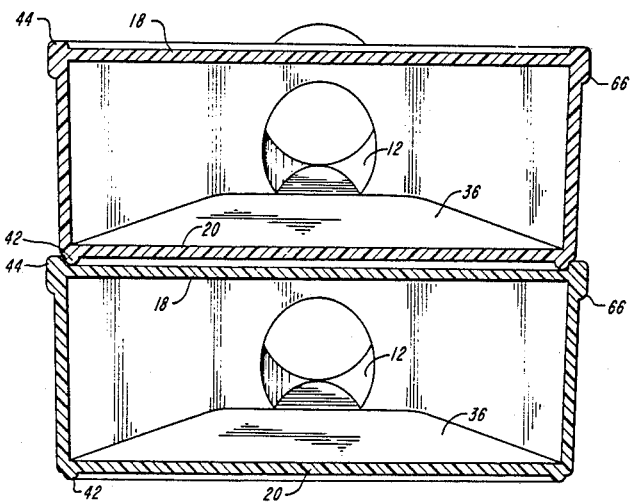
FIG. 8 is a rear view of the stack shown in FIG. 7.

In FIGS. 6–8, the rectangular portion 34 of the bottom wall 16 is shown to carry a downwardly extending bead 42 about its periphery, which functions as one part of a stacking facility provided in the flask to enable identical flasks to be stacked compactly and positively with one another. The stack is shown in FIGS. 7 and 8. The other part of the stacking facility is in the form of an upwardly extending flange 44 formed about the edge of the top wall 18. Because the plan dimensions of the top wall 18 slightly exceed the corresponding dimensions of the bottom wall 16, when one flask is stacked upon another as shown in FIGS. 7 and 8, the bead 42 on the bottom wall just fits within the flange 44 on the top wall. Additional stability is afforded the stack by the short rib 46 on the top wall adjacent to the rear wall 24 and spaced from the flange 44 a distance just sufficient to receive the bead 42 of the bottom wall between them. This feature is shown in FIG. 7. The small interruption 48 in the flange 44 (see FIGS. 1 and 5) is to prevent a vacuum when stacked or placed on a wet surface and in no way affects the stacking facility.

In FIG. 1, a large frosted area 50 is shown on the side wall 22 and the portion 32 of the end wall 26. The frosted portion provides a large labeling surface for use in the laboratory. The top wall 18 is also shown to carry alpha-numeric coordinates along one side and across the width of the flask adjacent the side wall 22 and second end wall 26. The letters and numbers are molded in the surface to simplify microscope work by providing a ready means for identifying culture locations growing in the flask.

The neck 12 of the flask carries an interrupted thread 56 on its outer surface 58 adjacent its open end 60. The interrupted thread 56 cooperates with mating threads 61 in cap 14 so that the cap may form a leak proof seal against the end surface 62. To form the leak proof seal, a rubber lining 63 may be provided within the cap across the top wall 64 thereof.

The flask is injection molded in two parts from a clear plastic material such as a polysterene. One part of the flask includes the bottom wall 16, side walls 20 and 22, end walls 24 and 26, and neck 12. The other part comprises the top wall 18, a short skirt 66 that fits over the top edges of the side and end walls 20, 22, 24 and 26, and a generally semi-circular collar 70 that surrounds the upper half of neck 12 as is shown in FIGS. 1, 2 and 4. The collar 70 assists in positioning the top wall and skirt on the bottom part of the container when the two are cemented or otherwise secured together in sealed relationship. The collar 70 also serves to strengthen the connection between the neck 12 and the second end wall 26. It will be appreciated that a slight draft is provided in the side walls 20 and 22 and end walls 24 and 26 to facilitate removal of the lower part of the container from the mold during manufacture. This in turn results in the slightly larger surface for top wall 18 so as to provide a firm seat for the bottom wall of another flask when one is stacked upon another.

The configuration of the flask and more particularly the canted neck 14 with its flat 38 and the ramp 36 provide several advantages. It will be noted in the drawings that the width of the neck is larger than the height of the central portion 28 of the end wall 26. This extra wide neck along with the shape of the flask itself provides access to all four bottom corners 72, 74, 76 and 78 with a scraper. The neck width will also permit a pipette to reach the four corners 74, 76, 80 and 82 of end wall 24 so as to remove medium from the bottom when the flask is placed on end as shown in FIG. 4. Furthermore, the ramp angle minimizes the possibility of medium in the bottle flowing into the neck 12. Also, the canted neck and ramp prevent fluid retention when pouring medium into or out of the flask. The ramp also provides a dam to prevent puddles on the bottom wall 16 from flowing out the neck. In addition, the neck angle provides maximum neck and cap diameter with the given flask thickness without interfering with the stackability of the containers (see FIGS. 7 and 8). It should also be noted that the corners of the flask are all rounded so as not to tear the sterile wrap (not shown) in which the unit is normally packaged.

Having described this invention in detail, those skilled in the art will appreciate that numerous modifications may be made thereof without departing from its spirit. Therefore, it is not intended that the breadth of this invention be limited to the specific embodiments illustrated and described. Rather, the scope of this invention is to be determined by the appended claims and their equivalents.

I claim:

1. A laboratory flask comprising
   a body having top and bottom walls joined by two side walls and first and second end walls, said bottom wall having a main portion generally parallel to the top wall,
   a neck providing access to the body open at one end and connected at its other end to the second end wall and canted upwardly therefrom toward its open end, said neck being circular at said open end,
   and a ramp forming part of the bottom wall adjacent the second end wall and extending upwardly from the plane of the main portion of the bottom wall, and forming an obtuse angle therewith, toward the plane of the top wall and joining the second end wall,
   said neck having top and bottom sides which diverge from one another in the direction of the open end and coaxial cylindrical side walls which terminate in said circular open end, said top and bottom sides of the neck being connected to the second end wall immediately adjacent the top and bottom edges thereof.

2. A laboratory flask as defined in claim 1 further comprising
   coordinate markings on the top wall of the body for identifying the location of cultures growing in the flask on the bottom wall.

3. A laboratory flask as defined in claim 1 wherein said flask is molded of a transparent plastic,
   and a frosted labeling surface is provided on one of the side walls and an end wall.

4. A laboratory flask as defined in claim 1 wherein the main portion of the bottom wall is rectangular and the ramp is a trapezoid.

5. A laboratory flask as defined in claim 1 further characterized by
   said neck being externally threaded at its open end, and a screw cap for the flask.

6. A laboratory flask as defined in claim 1 wherein the width of the neck at the second end wall exceeds the height of said second end wall where the neck is connected to said second end wall.

7. A laboratory flask as defined in claim 1 further comprising
   stacking means provided on the top and bottom walls enabling identical flasks to be stacked one upon the other with the bottom wall of one flask resting on the top wall of a second flask.

8. A laboratory flask as defined in claim 7 wherein said stacking means includes an upwardly extending flange formed on the top wall at its periphery and a downwardly extending bead formed on the main portion of the bottom wall just inwardly of its periphery so that when identical flasks are stacked the bead of the upper flask sits immediately within the flange on the lower flask.

9. A laboratory flask as defined in claim 1 wherein the bottom wall, side walls, and end walls and the neck are molded as a unitary structure and the top wall is separately molded and sealed to the side walls and the end walls about it periphery.

10. A laboratory flask as defined in claim 9 wherein the side and end walls diverge upwardly from one another.

11. A laboratory flask as defined in claim 1 wherein said neck has a planar area of the bottom side and converges toward the top side of the neck in the direction of the second wall.

12. A laboratory flask as defined in claim 11 wherein the main portion of the bottom wall is rectangular and the ramp is a trapezoid,
    and said top wall is planar and has the same shape and size in plan as the bottom wall.

13. A laboratory flask as defined in claim 11 wherein the planar area in the neck extends the full length thereof and diminishes in width from the end of the neck connected to the second end wall toward its open end.

14. A laboratory flask as defined in claim 13 wherein the open end of the neck extends upwardly above the plane of the top wall.

15. A laboratory flask as defined in claim 14 further comprising
a cover-all cap for closing the open end of the neck,
and stacking means provided on the top and bottom walls enabling identical flasks to be stacked with the bottom wall of one resting on the top wall of a second flask and with the cover-all caps in place on the necks.

16. A laboratory flask comprising
a body having top and bottom walls joined by two side walls and first and second end walls, said bottom wall having a main portion generally parallel to the top wall,
a neck providing access to the body open at one end and connected at its other end to the second end wall and canted upwardly therefrom toward its open end,
and a ramp forming part of the bottom wall adjacent the second end wall and extending upwardly from the plane of the main portion of the bottom wall toward the plane of the top wall and joining the second end wall,
said neck having top and bottom sides which diverge from one another in the direction of the open end, and coaxial cylindrical side walls which terminate in said circular open end said top and bottom sides of the neck being connected to the second end wall immediately adjacent the top and bottom edges thereof,
said neck also having a planar area on the bottom side and converging toward the top side of the neck in the direction of the second wall, said neck being circular at its open end,
said ramp being inclined at an angle of approximately 22° with the plane of the main portion of the bottom wall.

17. A laboratory flask as defined in claim 16 further comprising
the planar area being inclined upwardly from the upper end of the ramp at an angle of approximately 8° with the plane of the main portion of the bottom wall.

18. A laboratory flask as defined in claim 17 further comprising
said second end wall having a central portion to which the neck is connected and side portions which diverge from one another toward the first end wall at an angle of approximately 90°.

19. A laboratory flask comprising
a body having top and bottom walls joined by two side walls and first and second end walls,
a neck providing access to the body open at one end and connected at its other end to the second end wall and canted upwardly therefrom toward its open end, said neck being circular at said open end,
said neck having top and bottom sides which diverge from one another in the direction of the open end and coaxial cylindrical side walls which terminate in said circular open end, the bottom side of the neck being inclined upwardly at an angle of approximately 8° with the plane of the bottom wall.

20. A laboratory flask as defined in claim 19 further comprising
said second end wall having a central portion to which the neck is connected and side portions which diverge from one another toward the first end wall at an angle of approximately 90°.

21. A laboratory flask as defined in claim 19 wherein
said neck has a planar area on the bottom side and converges toward the top side of the neck in the direction of the second wall.

22. A laboratory flask as defined in claim 21 wherein
the planar area in the neck extends the full length thereof and diminishes in width from the end of the neck connected to the second end wall toward its open end.

23. A laboratory flask as defined in claim 21 wherein
said bottom wall has a main portion nearer the first end wall and parallel to the top wall, and wherein said bottom wall also has a ramp near the second end wall and extending upwardly from the plane of the main portion and joining the second end wall.

24. A laboratory flask as defined in claim 19 wherein
said bottom wall has a main portion nearer the first end wall and parallel to the top wall, and wherein said bottom wall also has a ramp near the second end wall and extending upwardly from the plane of the main portion and joining the second end wall.

25. A laboratory flask as defined in claim 24 further comprising
said ramp being inclined at an angle of approximately 22° with the plane of the main portion of the bottom wall.

26. A laboratory flask as defined in claim 25 further comprising
said ramp being inclined at an angle of approximately 22° with the plane of the main portion of the bottom wall.

* * * * *